(12) United States Patent
Paska (10) Patent No.: US 11,965,867 B2
(45) Date of Patent: Apr. 23, 2024

(54) SENSING ELEMENT FOR CHEMIRESISTOR SENSOR AND METHOD OF MAKING SAME

(71) Applicant: NanoScent Ltd., Mishgav (IL)

(72) Inventor: Yair Paska, Kiryat Ata (IL)

(73) Assignee: NanoScent Ltd., Mishgav (IL)

( * ) Notice: Subject to any disclaimer, the term of this patent is extended or adjusted under 35 U.S.C. 154(b) by 638 days.

(21) Appl. No.: 17/257,030

(22) PCT Filed: May 28, 2019

(86) PCT No.: PCT/IL2019/050608
§ 371 (c)(1),
(2) Date: Dec. 30, 2020

(87) PCT Pub. No.: WO2020/016876
PCT Pub. Date: Jan. 23, 2020

(65) Prior Publication Data
US 2021/0231627 A1    Jul. 29, 2021

Related U.S. Application Data

(60) Provisional application No. 62/698,315, filed on Jul. 16, 2018.

(51) Int. Cl.
*G01N 27/12* (2006.01)
*B33Y 10/00* (2015.01)
(Continued)

(52) U.S. Cl.
CPC .......... *G01N 33/0031* (2013.01); *B33Y 10/00* (2014.12); *B33Y 50/00* (2014.12); *B33Y 80/00* (2014.12); *G01N 27/127* (2013.01)

(58) Field of Classification Search
CPC .. G01N 33/0031; G01N 27/127; B33Y 50/00; B33Y 80/00
See application file for complete search history.

(56) References Cited

U.S. PATENT DOCUMENTS 6,458,327 B1    10/2002    Vossmeyer
2003/0082237 A1    5/2003    Cha et al.
(Continued)

FOREIGN PATENT DOCUMENTS

WO    WO 2018/172450    9/2018

OTHER PUBLICATIONS

Internarnational Search Report of Application No. PCT/IL2019/050608 dated Sep. 22, 2019.

*Primary Examiner* — Jill A Warden
*Assistant Examiner* — Michael Stanley Gzybowski
(74) *Attorney, Agent, or Firm* — The Roy Gross Law Firm, LLC; Roy Gross (57) ABSTRACT

A sensing element for a chemiresistor sensor and a method of making such a sensing element is disclosed. The sensing element may include: one or more first type of 3D elements, each comprising a first type of chemiresistor particles; and one or more second type of 3D elements, each comprising a second type of chemiresistor particles. At least one of the one or more first type of 3D elements and at least one of the one or more second type of 3D elements may have one or more joint surface. The first type of chemiresistor particles may differ from the second type of chemiresistor particles by at least one of: a type of nanoparticle core and a type of organic ligands bonded to each nanoparticle core.

12 Claims, 5 Drawing Sheets

(51) Int. Cl.
*B33Y 50/00* (2015.01)
*B33Y 80/00* (2015.01)
*G01N 21/77* (2006.01)
*G01N 33/00* (2006.01)
*H01L 51/05* (2006.01)

(56) References Cited

U.S. PATENT DOCUMENTS

| | | |
|---|---|---|
| 2009/0049890 A1 | 2/2009 | Zhong et al. |
| 2010/0225337 A1* | 9/2010 | Zamborini ............ G01N 27/127 977/773 |
| 2010/0273665 A1 | 10/2010 | Haick et al. |

* cited by examiner

SENSING ELEMENT FOR CHEMIRESISTOR SENSOR AND METHOD OF MAKING SAME

CROSS-REFERENCE TO RELATED APPLICATIONS

This application is a National Phase Application of PCT International Application No. PCT/IL2019/050608, International Filing Date May 28, 2019, claiming the benefit of U.S. Provisional Patent Application No. 62/698,315, filed Jul. 16, 2018 which are hereby incorporated by reference.

FIELD OF THE INVENTION

The present invention generally relates to chemiresistor sensors. More particularly, the present invention relates to sensing elements for chemiresistor sensors and method of making such sensing elements.

BACKGROUND OF THE INVENTION

Chemiresistor sensors are sensors that can detect the presence of volatile compound (VCs). A chemiresistor sensor includes a material or structure that changes its electrical resistance in response to changes in the nearby chemical environment, for example, due to the presence of VCs. Commercial chemiresistor sensors for sensing VCs include a sensing element made from one of: carbon nanotubes, graphene, carbon nanoparticles and the like. Another optional sensor includes a sensing element made form metallic nanoparticles cores coated with organic ligands. The organic ligands are bonded to the surface of the metallic core at one end and are configured to be weakly bonded (e.g., interact) to a VC at the other end. The most suitable and widely used cores are nanoparticles of: Au, Pt, Pd Ag and further also alloys consisting of Ni, Co, Cu, Al, Au/Ag, Au/Cu, Au/Ag/Cu, Au/Pt, Au/Pd, Au/Ag/Cu/Pd, Pt/Rh, Ni/Co, and Pt/Ni/Fe.

The most common type of organic ligands that can bond with the surface of a metallic particle having one of the above listed metallic cores is thiol (sulfides). Thiols can be bonded with the metallic cores via functional groups such as: alkylthiols with C3-C24 chains, ω-functionalized alkanethiolates, arenethiolate, (γ-mercaptopropyl) tri-methyloxysilane, dialkyl disulfides, xanthates, oligonucleotides, polynucleotides, peptides, proteins, enzymes, polysaccharides, and phospholipids.

Each particle in a chemiresistor sensor may interact with more than one types of VC. However, the specific chemical—physical nature of each particle, in particular the functional groups in the organic ligands makes each of them capable of forming larger number of weak bonds with a major (e.g., favorable) type of VC. However, other VCs may also be weakly bonded to the ligands. The VC may interact or absorb in several sites of the nanoparticle, for example, core surface, bonding group, the functional groups and the like. Sensing elements known in the art usually includes a single type of particle. In such case each sensing element may be sensitive to or detect a single type of VC or may detect two types of VC, but without the ability to simultaneously and in real time separate between the two types of particles.

Accordingly, there is a need for a sensing element for chemiresistor sensors that may allow to controllably detect two or more VCs simultaneously and in real time in a single sensing element while avoiding any mutual effect or disturbances.

SUMMARY OF THE INVENTION

Some aspects of the invention may be related to a sensing element for a chemiresistor sensor. In some embodiments, the sensing element may include: one or more first type of 3D elements, each comprising a first type of chemiresistor particles; and one or more second type of 3D elements, each comprising a second type of chemiresistor particles. In some embodiments, at least one of the one or more first type of 3D elements and at least one of the one or more second type of 3D elements may have one or more joint surface. In some embodiments, the first type of chemiresistor particles may differ from the second type of chemiresistor particles by at least one of: a type of nanoparticle core and a type of organic ligands bonded to each nanoparticle core.

In some embodiments, the one or more first type of 3D elements and the one or more second type of 3D elements may form a multilayered 3D structure. In some embodiments, multilayered 3D structure may include alternating layers each including either the first or the second type of chemiresistor particles. In some embodiments, at least one layer in the multilayered 3D structure comprises a chessboard like structure made from alternating cube shaped 3D elements each comprising either the first type of chemiresistor particles or the second type of chemiresistor particles.

In some embodiments, a first nanoparticle core of the first type of 3D elements differs from a second nanoparticle core of the second type of 3D elements by at least one of: the type of conductive material, the size of the core particle and the shape of the core particle. In some embodiments, the first type of chemiresistor particles may include a first type of organic ligands and the second type of chemiresistor particles comprises a second type of organic ligands. In some embodiments, the first type of organic ligands may differ from the second type of organic ligands by the type of functional groups included in each type of organic ligands.

In some embodiments, the sensing element may further include: one or more third type of 3D elements comprising a third type of chemiresistor particles. In some embodiments, the one or more third type of 3D elements may have one or more joint surfaces with at least one of the one or more first and second types of 3D elements. In some embodiments, the third type of chemiresistor particles may differ from the first and the second types of chemiresistor particles by at least one of: a nanoparticle core and organic ligands bonded to each nanoparticle core.

In some embodiments, the first type of chemiresistor particles may be selected to interact with at least one first major type of volatile compound (VCs) and the second type of chemiresistor particles may be selected to interact with at least one second major type of VCs. In some embodiments, the first type of 3D elements may differ from the second type of 3D elements by the porosity between the chemiresistor particles included in each type of 3D element.

Some aspects of the invention may be related to chemiresistor sensor, including: two electrodes; and a sensing element. In some embodiments, the sensing element may include: one or more first type of 3D elements, each comprising a first type of chemiresistor particles; and one or more second type of 3D elements, each comprising a second type of chemiresistor particles. In some embodiments, at least one of the one or more first type of 3D elements and at least one of the one or more second type of 3D elements may have one or more joint surface. In some embodiments, the first type of chemiresistor particles may differ from the second type of chemiresistor particles by at least one of: a type of nanoparticle core and a type of organic ligands bonded to each nanoparticle core.

In some embodiments, a first electrode may have at least one first joint surface with both at least one of the one or more first type of 3D elements and at least one of the one or more second type of 3D elements; and a second electrode may have at least one second joint surface with both at least one of the one or more first type of 3D elements and at least one of the one or more second type of 3D elements.

In some embodiments, a first electrode may have at least one first joint surface with at least one of the one or more first type of 3D elements but not with any one of the one or more second type of 3D elements; and a second electrode may have at least one second joint surface with both at least one of the one or more first type of 3D elements but not with any one of the one or more second type of 3D elements.

Some additional aspects of the invention may be related to a method of making a sensing element for chemiresistor sensor. In some embodiments, the method may include: receiving a 3D model comprising one or more first type of 3D elements and one or more second type of 3D elements having one or more joint surfaces; and depositing, on a substrate, a 3D structure according to the received 3D model, layer by layer using a first ink for forming the one or more first type of 3D elements and a second ink for forming the one or more second type of 3D elements. In some embodiments, the first ink may include: a first solvent and a plurality of first type of chemiresistor particles and the second ink may include a second solvent and a plurality of second type of chemiresistor particles. In some embodiments, the first type of chemiresistor particles may differ from the second type of chemiresistor particles by at least one of: a nanoparticle core and organic ligands bonded to each nanoparticle core.

In some embodiments, depositing may be done by a computerized printer. In some embodiments, receiving the 3D model may include: receiving a request to distinguish between at least two defined volatile compounds (VCs); and determining the first type of 3D elements and the second type of 3D elements according to the received request. In some embodiments, the determining may include selecting the first type of chemiresistor particles to be configured to interact with a first defined major type of VC and the second type of chemiresistor particles to be configured to interact with a second defined major type of VC.

In some embodiments, the method may further include: adding a first electrode having at least one first joint surface with both at least one of the one or more first type of 3D elements and at least one of the one or more second type of 3D elements; and adding a second electrode having at least one second joint surface with both at least one of the one or more first type of 3D elements and at least one of the one or more second type of 3D elements.

In some embodiments, the method may further include: a first electrode having at least one first joint surface with at least one of the one or more first type of 3D elements but not with any one of the one or more second type of 3D elements; and adding a second electrode having at least one second joint surface with both at least one of the one or more first type of 3D elements but not with any one of the one or more second type of 3D elements.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Aspects of the invention may be directed to a sensing element for chemiresistor sensors that may be capable of interacting with at least two different VCs while avoiding any undesired influences, for example, from other VCs, such as, water. VC according to embodiments of the invention may include any compound either organic or inorganic that may be configured to be evaporated (to some extant) in room temperature. For example, VC may include: water (e.g., humidity), ammonia, urea, aromatic compounds, acetone and the like.

A sensing element according to embodiments of the invention may include at least two different types of sensing particles. Each type of sensing particle may be configured to interact with one major type of VC (but also with minor amounts of other VCs). As used herein, a major type of VC may include a specific chemical compound (e.g., ammonia) or a family of chemical compounds (e.g., alcohols, ketones, amines, anhydride, esters, aldehydes, ethers, light gas, aromatics and the like). In some embodiments, the types of chemiresistor particles may differ from one another by at least one of: a type of nanoparticle core and a type of organic ligands bonded to each nanoparticle core. In some embodiments, each type of sensing element may be included in a different 3D element or elements. Therefore, a sensing element according to embodiments of the invention may include a 3D structure that may include at least two different 3D elements, each 3D element includes different type of chemiresistor particles.

The chemiresistor particles according to embodiments of the invention may include nanoparticle cores made from novel conductive material that may include any suitable metals, alloys or conducting oxides. As used herein, an alloy may be defined as a metal that includes a primary metallic element (e.g., Ir and Ru) being the major component (e.g., by wt. %) mixed with any additional element, either metallic or nonmetallic. For example, Ir alloy may include a mixture of Ir being the major component with, Pd, Ru, Au, Pt, Ag and the like. In some embodiments, each nanoparticle core may be coated with organic ligands, for example, thiols. Other organic ligands may be used, if each nanoparticle core may further be at least partially coated with an oxide layer, for example, at least one of: $IrO_x$ and $RuO_x$. In some embodiments, such an oxide layer may allow bonding additional organic ligands, such as, diazoniums, silanes, carboxylic acids, tri-chloro, methoxy, ethoxy, tri hydroxide, di-chloro, chloro and the like. In some embodiments, these organic ligands may form much stronger bonds with the oxide layer on the nanoparticle core than the bonds thiol form on any of the nanoparticle cores known in the art. In some embodiments, the oxide layer may prevent any further oxidation of the core nanoparticle, making the core nanoparticle stable in air (e.g., in the presence of oxygen).

In some embodiments, each organic ligand may further include one or more functional groups configured to interact with VCs via hydrogen, Van Der Waals (VDW) bonds, Pi-Pi orbital interaction (for aromatics), dipole-dipole interaction (for polar), steric interference, charge to charge interaction, coordination bond and the like. For example, the organic ligands may include OH groups or N groups configured to interact with water. In another example, the organic ligands may include benzene ring configured to interact with aromatic VCs. In yet another example, the organic ligands may include ionic or charged functional groups configured to interact with ionic VC, such as acids (e.g., citric acid, etc.).

Reference is now made to FIGS. 1A, 1B, 1C and 1D which are illustrations of particles for a sensing element for a chemiresistor sensor according to some embodiments, of the invention. In some embodiments, each one of particles 10, 20, 30 and 40 may include: a nanoparticle core 12, 22, 32 and 42 respectively. Nanoparticle cores 12, 22, 32 and 42 may be made from a conductive material selected from a group consisting of: Ir, Ir-alloy, $IrO_x$, Ru, Ru-alloy, $RuO_x$ Au, Pt, Pd, Ag, Ni, Co, Cu, Al, Au/Ag, Au/Cu, Au/Ag/Cu, Au/Pt, Au/Pd, Au/Ag/Cu/Pd, Pt/Rh, Ni/Co, Pt/Ni/Fe and any combination thereof. In some embodiments, nanoparticle cores 12, 22, 32 and 42 may be made from any conductive metallic oxide. In some embodiments, the average diameter of nanoparticle cores 12, 22, 32 and 42 may be of at most 100 nm, for example, 50 nm, 20 nm, 10 nm, 5 nm and 1 nm.

In some embodiments, nanoparticle core 12 may include a single metal or alloy and may have crystalline structure. In some embodiments, nanoparticle core 22 may include a single metal or alloy and may have an amorphous structure. In some embodiments, nanoparticle cores 32 and 42 may include more than one metal or alloy, for example, nanoparticle cores 32 and 42 may include matrixes 33 and 43 respectively form a first material (e.g., a conductive oxide such as $RuO_x$, $IrO_x$) and one or more precipitate 34 and 44 from a second material (e.g., Ru alloy, Ru, Ir alloy, Ir). In some embodiments, matrix 33 may have a crystalline structure and matrix 43 may have an amorphous structure.

In some embodiments, each one of particles 10, 20, 30 and 40 may further include a plurality of organic ligands 16, 26, 36 and 46, respectively, bonded, for example, via covalent bonds, from one side to the metallic core and capable of interacting with a VC. In some embodiments, the organic ligands are selected from a group consisting of: thiols, diazoniums, silanes, carboxylic acids, tri-chloro, methoxy, ethoxy, tri hydroxide, di-chloro, chloro and the like. In some embodiments, more than one type of organic ligand may be bonded with one of cores 10, 20, 30 and 40. For example, a core 10 that includes crystalline $RuO_x$ may be coated with organic ligands 16 of methoxy silane and trichloro silane. Some examples for organic ligands according to some embodiments of the invention are given in the table of FIG. 2. The organic ligands presented in FIG. 2 can bond from one side, the side that includes the bonding group, for example, the chloro-silane, group with the surface of cores 10, 20, 30 and 40, and from the other side (marked as X) with a VC, for example, a specific functional group can be added to the ligand chain that is configured to target (e.g., interact with) a specific VC. In some embodiments, the VC may interact with the branch of the organic ligands, for example, via VDW bonds, hydrogen bonds, Pi-Pi orbital interaction (for aromatics), dipole-dipole interaction (for polar), steric interference, charge to charge interaction, coordination bond, etc.

In some embodiments, nanoparticle cores 10, 20, 30 and 40 may at least be partially covered with a conductive oxide layer 18, 28, 38 and 48 respectively, including at least one of: $IrO_x$ and $RuO_x$ or any other conductive oxides. In some embodiments, when nanoparticle cores 10, 20, 30 and 40 include crystalline or amorphous Ir, Ir-alloy, Ru and Ru-alloy, a thin oxidation layer may form on at least a portion of the surface of nanoparticle cores 10, 20, 30 and 40. The thin oxidation layer may be formed due to the exposure of the nanoparticle cores to air or oxygen. The thickness of the oxidation layer may be of few nanometers, for example, a native oxide layer of 1-2 nm. In some embodiments, such an oxidation layer may allow stronger bonding between organic ligand 16, 26, 36 and 46 and the surface of cores 10, 20 30 and 40.

Figure 3A:
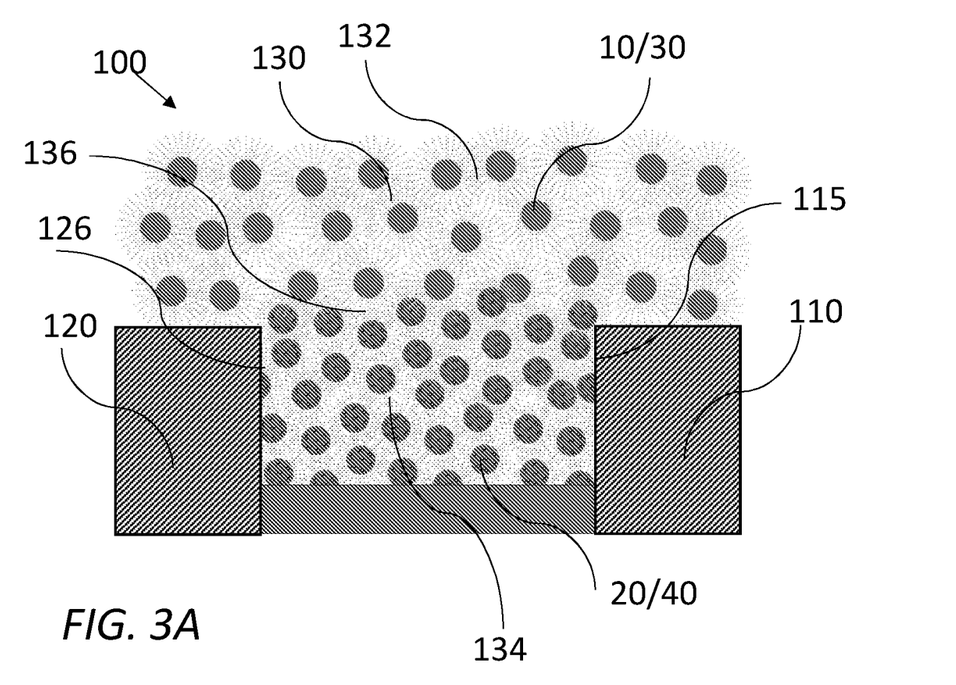
FIGS. 3A-3B are illustration of chemiresistor sensors according to some embodiments of the invention.

Reference is now made to FIG. 3A which is an illustration of a chemiresistor sensor according to some embodiments of the invention. A chemiresistor sensor 100 may include: two electrodes 110 and 120 and a sensing element 130. Sensing element 130 may include one or more first type of 3D elements 132, each including a first type of chemiresistor particles, for example, particles 10 or 30. Sensing element 130 may further include one or more second type of 3D elements 134, each including a second type of chemiresistor particles, for example, particles 30 or 40. In some embodiments, at least one of the one or more first type of 3D elements 132 and at least one of the one or more second type of 3D elements 134 may have one or more joint surfaces 136. As used herein, a joined surface is a surface at which the first type of particles from the first type of 3D element are in a physical contact with the second type of particles from the second type of 3D element or in a physical contact with the atoms included in an outer surface of an electrode.

In some embodiments, first type of 3D elements 132 differs from second type of 3D elements 134 by the porosity between the chemiresistor particles included in each type of element. The difference in porosity levels may occur due to the different lengths of the organic ligands (e.g., C3-C24) the size of the core particle, the functional groups added to the ligands and the like. Furthermore, difference in porosity levels may occur due to the selection of deposition parameters of an ink forming the 3D element (e.g., using inkjet printer), for example, the solvent viscosity, solvent selection, drying process, etc., that may result difference is the sensing element morphology.

In some embodiments, particles, such as particles 10 or 30, included in one or more 3D elements 132 may differ from particles, such as particles 20 or 40, included in one or more 3D elements 132 by at least one of: the core and the type of ligands. In some embodiments, the particles may differ in the cores' material (e.g., the type of metal, alloy or conductive oxide), the cores' structure (e.g., crystalline or amorphous), cores' size, cores' shape (e.g., sphere, cube, etc.) and the like. In some embodiments, the particles may differ in the type of ligands as listed herein above. In some embodiments, the types of organic ligands may differ by the type of functional groups included in each type of organic ligands. For example, one or more 3D elements 132 may include particles having Ru-alloy core coated with silanes ligands and one or more 3D elements 134 may include particles having Pt-alloy cores coated with thiol ligands.

In some embodiments, it may be required to sense only a first major type of VC while avoiding receiving signals (e.g., filtering) from at least one other type of major VC. As used herein, a major type of VC is a VC having a chemical structure to which a chemiresistor particle is designed to have a specific chemical-physical nature, (e.g., the functional groups in the organic ligands) which makes the particle capable of forming larger number of weak bonds with the major (e.g., favorable) VC. For such purpose a sensing element having the configuration of sensing element 130 may be used. Such sensing element 130 may have one or more 3D elements 132 configured to interact with the undesired major type of VC (e.g., water) and one or more 3D elements 134 configured to interact with the desired major type of VC (e.g., ammonia). Accordingly, water molecules may be captured and interact mainly with one or more 3D elements 132 and ammonia molecules may be captured and interact mainly with one or more 3D elements 134. In order to prevent sensor 100 from detecting the presence of water molecules, the current flowing between electrodes 110 and 120 must not pass through one or more 3D elements 132. The current may pass through the shortest possible passage between electrodes 110 and 120, therefore, in the configuration of sensor 100, when electrodes 110 and 120 have joint surfaces 116 and 126 respectively with one or more 3D elements 134, the current may pass via one or more 3D elements 134, but not via one or more 3D elements 132. Therefore, any conduction/resistance changes, occurred due to the interaction of VC molecule with the organic ligand, may be detected in one or more 3D elements 134 while one or more 3D elements 132 acting as a filter, for example, for water molecules. In another example, one or more 3D elements 132 may be configured to mainly interacted with acetone and one or more 3D elements 134 may be configured to mainly interact with urea. Therefore, sensor 100 may be configured to detect mainly presence of urea while filtering the influence of acetone.

Accordingly, in some embodiments, first electrode 110 may have at least one first joint surface 116 with one or more 3D elements of one type 134 but not with any one of the one or more of 3D elements of another type 132. In some embodiments, second electrode 120 may have at least one second joint surface 126 with at least one of the one or more types of 3D elements 134 but not with any one of the one or more 3D elements 132.

Figure 3B:
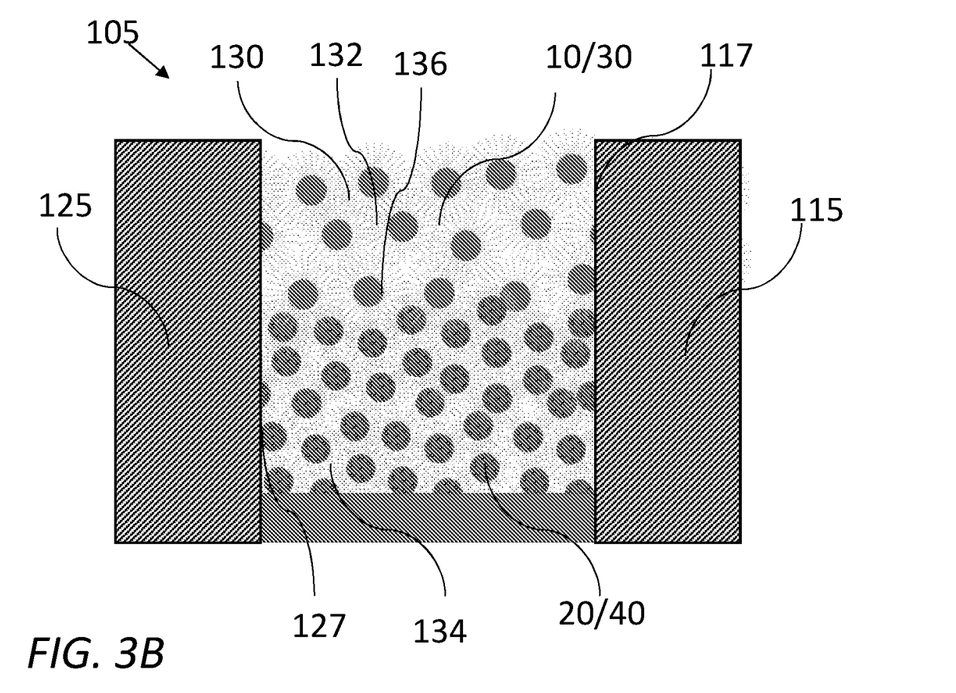

Reference is now made to FIG. 3B which is an illustration of a chemiresistor sensor according to some embodiments of the invention. A chemiresistor sensor 105 may include: two electrodes 115 and 125 and a sensing element 130. Sensing element 130 may have substantially the same structure as sensing element 130 disclosed with respect to sensor 100 and FIG. 3A.

In some embodiments, it may be required to sense two specific major types of VCs. For such purpose a sensing element having the configuration of sensing element 130 may include one or more 3D elements 132 configured to interact with a first major type of VC (e.g., urea) and one or more 3D elements 134 configured to interact with a second major type of VC (e.g., ammonia). Accordingly, for example, urea molecules may be captured and/or may interact mainly with one or more 3D elements 132 and, for example, ammonia molecules may be captured and/or may interact mainly with one or more 3D elements 134.

In some embodiments, in order to receive signals from both one or more 3D elements 132 and 134 the current may pass through both elements, therefore, electrodes 115 and 125 may have joint surfaces with at least one element from one or more 3D elements 132 and with at least one element from one or more 3D elements 134. In some embodiments, first electrode 115 may have at least one first joint surface 117 with both at least one of the one or more 3D elements 132 and at least one of the one or more 3D elements 134. In some embodiments, second electrode 125 may have at least one second joint surface 127 with both at least one of the one or more 3D elements 132 and at least one of the one or more 3D elements 134.

As should be understood by one skilled in the art the two 3D elements 132 and 134 having one joint surface 136, illustrated in FIGS. 3A and 3B are given as an example only. Other configuration having more than one 3D element 132 and more than one 3D elements 134 and therefore more than one joint surface 136 are illustrated and discussed with respect to FIGS. 4A, 4B and 4C, are also in the scope of the invention.

Figure 4A:
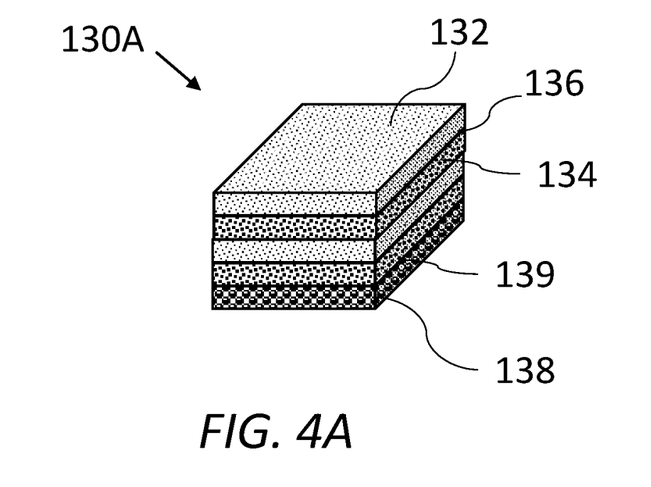
FIGS. 4A-4B are illustration of sensing elements according to some embodiments of the invention.
Figure 4B:
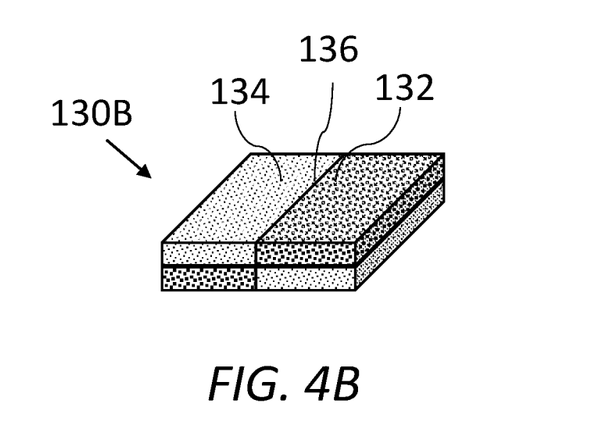
Figure 4C:
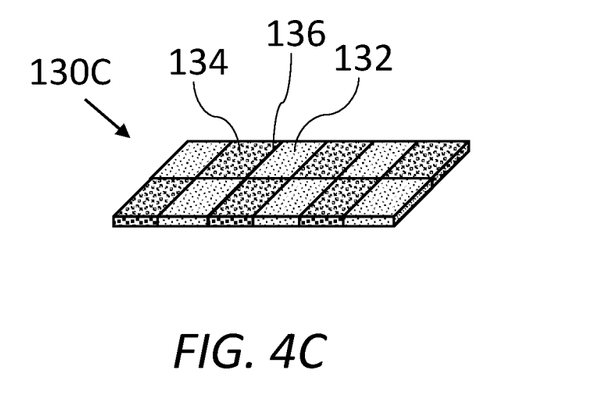

Reference is now made to FIGS. 4A, 4B and 4C which are illustrations of sensing elements according to some embodiments of the invention. Sensing elements 130A, 130B and 130C may include examples for different geometrical configurations having more than one element 132 and more than one element 134 therefore, more than one joint surface 136. As should be understood by one skilled in the art, sensing elements 130A, 130B and 130C are given as examples only and the invention is not limited to these specific geometrical configurations. In some embodiments, sensing element 130A may include a multilayered 3D structure. In some embodiments, the multilayered 3D structure may include alternating layers (e.g., 3D elements 132 and 134) each including either the first or the second types of chemiresistor particles. 3D elements 132 and 134 may have substantially the same microstructure as 3D elements 132 and 134 of sensing element 130 discussed hereinabove. In such configuration, sensing element 130A may be configured to interact, thus sense a first major type of VC and a second major type of VC. The highest amount of VCs may be captured and sensed in the two layers closer to the environment (e.g., the outer layers of elements).

In some embodiments, the sensing element (e.g., sensing element 130A) may include one or more third type of 3D elements 138 comprising a third type of chemiresistor particles. In some embodiments, one or more third type of 3D elements 138 may have one or more joint surfaces 139 with at least one of the one or more first and second types of 3D elements. In some embodiments, the third type of chemiresistor particles may differ from the first and the second types of chemiresistor particles by at least one of: a nanoparticle core and organic ligands bonded to each nanoparticle core.

In some embodiments, sensing element 130B may include a multilayered 3D structure having two different 3D elements 132 and 134 in the same layer. Therefore, in each layer a first portion of the layer may be configured to sense a first type of major VC and a second portion of the layer may be configured to sense a second major type of VC.

In some embodiments, sensing elements 130C may include at least one layer having a chessboard like structure made from alternating cube-shaped 3D elements 132 and 134 each comprising either the first type of chemiresistor particles or the second type of chemiresistor particles.

In some embodiments, each of sensing elements 130, 130A-130C may have dimensions of up to 5 mm×5 mm×100 microns. For example, the thickness of sensing elements 130, 130A-130C may be between 1-100 micron, e.g., up to 50 micron, 10 micron 5 microns or less. In some embodiments, the thickness of sensing elements 130, 130A-130C may be below 1 micron. In some embodiments, the thickness of sensing elements 130, 130A-130C may be above 1 nm.

In some embodiments, the sensing element may be fabricated by a 3D deposition system, such as an inkjet printer.

Figure 5:
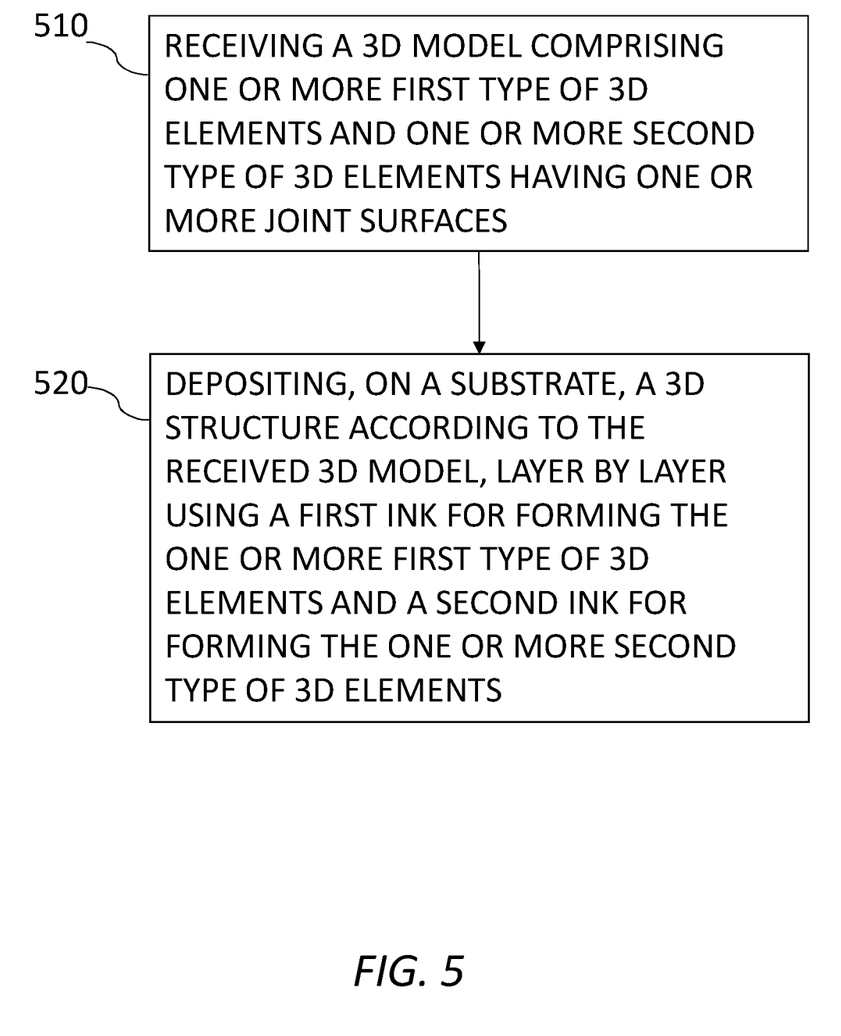
FIG. 5 is a flowchart of a method of making a sensing element for chemiresistor sensor according to some embodiments of the invention.

Reference is now made to FIG. 5 which is a flowchart of a method of making a sensing element for chemiresistor sensor. The method of FIG. 5 may be conducted by any computerized 3D deposition system, for example, computerized 3D inkjet printer, silk printer, die coating, Dr. baled and the like. The computerized 3D printer may be any 3D printer configured to deposit at least two types of ink according to a 3D model. In step 510, a 3D model may be received, for example, by a processor included in the 3D deposition system. The 3D model may include one or more 3D elements of a first type (e.g., elements 132) and one or more 3D elements of a second type (e.g., elements 134) having one or more joint surfaces (e.g., surfaces 136). In some embodiments, the 3D model may include partition of each 3D element in the first and second types of 3D elements into deposition layers. Each deposition layer may have a thickness of a single droplet. In some embodiments, each deposited layer may include portions of at least two different inks for forming two different 3D elements, as illustrated in FIGS. 4B and 4C. In some embodiments, each deposited layer may include a single type of ink for forming a single type of element, as illustrated in FIGS. 3A, 3B and 4A.

In some embodiments, a first ink, from the two or more different types of inks, may include: a first solvent and a plurality of chemiresistor particles of a first type and a second ink, from the two or more different types of ink, may include a second solvent and a plurality of chemiresistor particles of a second type. For example, the first type of solvent and the second type of solvent may be one of: toluene, ethanol, methanol, ethylbenzene, dichlorobenzene, hexyl acetate, anisole, phorone, chlorobenzene, acetone, diacetone alcohol, pentanone, ethyl acetate, butyl lactate, cyclohexanone, chloroform, water, glycol family and the like. In some embodiments, the first solvent may be different from the second solvent. In some embodiments, the first and second type of chemiresistor particles may be any one of the chemiresistor particles disclosed hereinabove, for example, particles 10, 20, 30 and 40.

In some embodiments, the first type of chemiresistor particles may differ from the second type of chemiresistor particles by at least one of: a nanoparticle core and organic ligands bonded to each nanoparticle core, as widely discussed with respect to FIGS. 1A, 1B, 1C, 1D and 3A. In some embodiments, the first and/or second inks may further include additives such as: sodium lauryl sulfate, 4-(1,1,3,3-Tetramethylbutyl)phenyl-polyethylene glycol, t-Octylphenoxypolyethoxyethanol, Polyethylene glycol tert-octylphenyl ether and the like.

In some embodiments, particles 10, 20, 30 and 40 may be made using several known in the art methods of bonding together conductive cores with organic ligands. For example, Nanoparticles cores (e.g., cores 12, 22, 32 and 42) made from a conductive material oxide may be obtained. In some embodiments, the nanoparticles cores may be commercially available for purchasing, either as crystalline, amorphous and/or as an alloy. In some embodiments, the nanoparticles cores may be prepared by, for example, a co-dispersion, and/or by ball milling and the like.

An example for preparing Ru or $RuO_x$, core particles may be include reduction of a salt of the required metal(s), e.g. $RuCl_3.xH_2O$ or similar, by the use of a suitable reducing agent such as sodium acetate, sodium or other borohydride, hydrazine, or any available known reducing agent. the materials may be held in aqueous solution and heated under reflux conditions or hydrothermal conditions, or by heating by microwave or other direct radiation. In these examples, depending on the process chosen, the metal salt and the reducing agent can be pre-mixed or mixed after heating to a desired temperature. Blending of the reducing agent with the metal salt, possibly with additional treatment such as heating/cooling, may lead to the formation of nucleated metal clusters that develop with time into nanoparticles in the reaction mixture. The growth of these particles may be controlled by one or more of: the type of ligands, reaction time, temperature, the presence of surface-active agents (surfactants) or other additives to moderate growth of the particles and the like.

In some embodiments, the rate of the reaction and the temperature may determine if a crystalline or amorphous structure is to be obtained. For example, using slow rate (e.g., reducing agent insertion to the reaction) and temperature in the range of 0-25° C. may result in amorphous structure, while using higher reaction rate and lower temperature (e.g., lower than 0° C.) may result in crystalline structure.

Figure 1A:
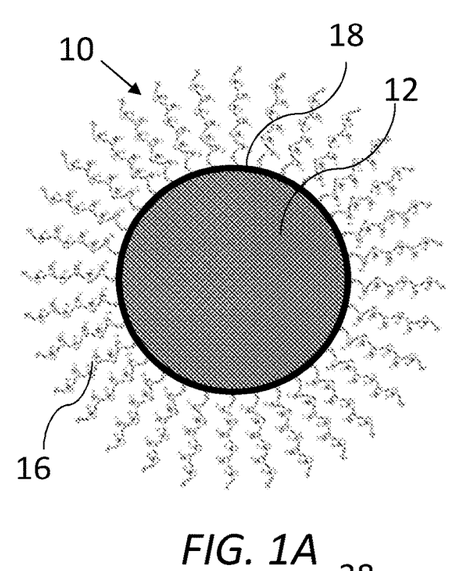
FIGS. 1A, 1B, 1C and 1D are illustrations of particles for chemiresistor sensor according to some embodiments of the invention.
Figure 1B:
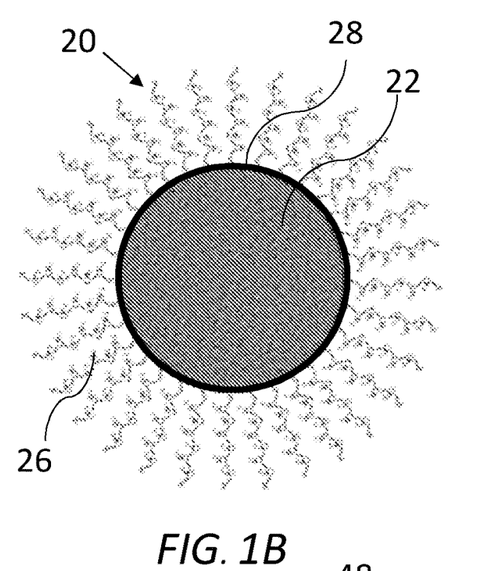
Figure 1C:
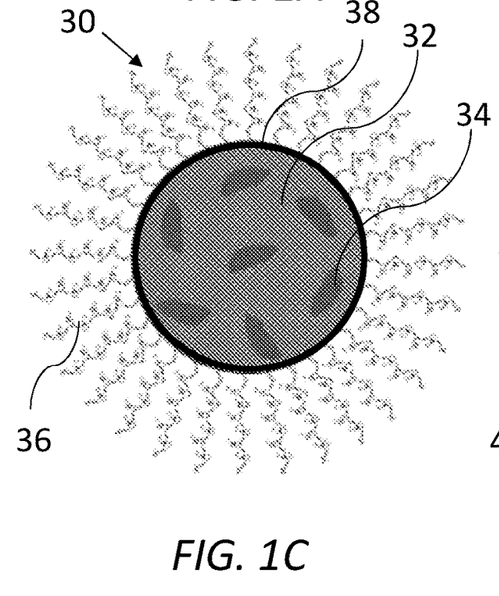
Figure 1D:
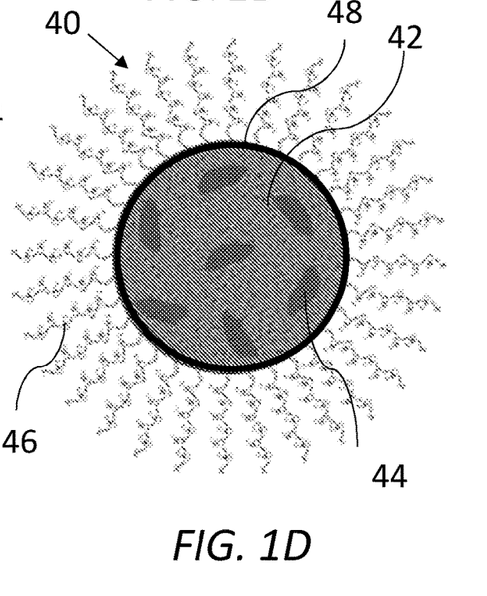
Figure 2:
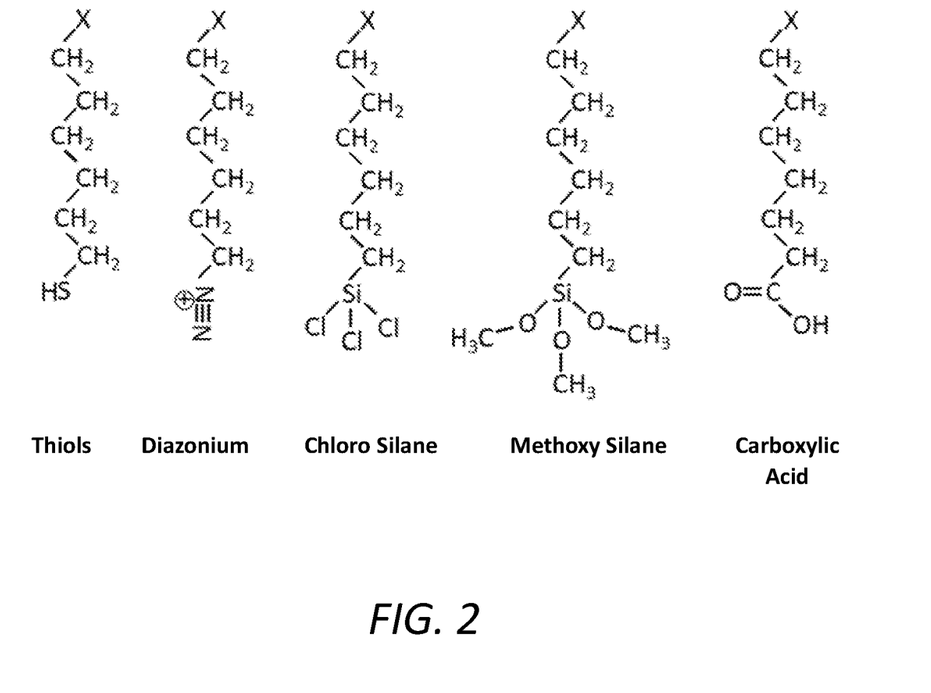
FIG. 2 is table illustrating optional ligands according to embodiments of the invention.

In some embodiments, a core (e.g., cores 32 and 42) having at least two types of materials may be prepared in a single step where salts of both materials are present in the reaction mixture. Such a one-step process (e.g., mixing the salts of different metals together) could lead either to alloys of the various particles, separate particles of one species and another, or a mixture of those.

In some embodiments, the plurality of organic ligands (e.g., organic ligands 16, 26, 36 and 46) may be bonded (e.g., covalently bonded) with the surface of the core nanoparticles. For example, dry powder core nanoparticles may be mixed with solvents and organic ligands (e.g., thiol, silane, and the like) and stirred together for a predetermined amount of time (e.g., 0.5-2 hours) at a predetermined temperature (e.g., 10, 20, 30 and 40° C.). In some embodiments, the solvent may be selected from a group consisting of: sodium acetate, sodium borohydride or hydrazine, or any other suitable solvent. In some embodiments, in order to disperse the dry core nanoparticles, methods such as, sonication, ultrasonic methods, homogenizing stirring method (e.g., using blades) and the like.

In step 520, a 3D structure may be deposited on a substrate (e.g., silicon) according to the received 3D model, layer by layer using the first ink for forming the one or more first type of 3D elements and the second ink for forming the one or more second type of 3D elements. For example, for ink-jet printing of element 130A illustrated in FIG. 4A one or more layers each including droplets from a first ink may be deposited for forming a first 3D element 132 and one or more layers each including droplets from a second ink may be deposited for forming a first 3D element 134, alternately repeating this the process until the 3D structure of element 130 may be deposited. In yet another example, two different inks may be deposited in the same layer for forming sensing elements 130B and 130C illustrated in FIGS. 4B and 4C. A print head included in the printer may be configured to deposit two types of ink in the same layer. For example, a first type of ink in a first portion of a layer included in sensing element 130B and a second type of ink in a second portion of a layer included in sensing element 130B. Each one of elements 132 and 134 included in sensing element 130B may be deposited using one or more of layers.

In some embodiments, the 3D model may be determined based on a request to detect one or more major type of VC. In some embodiments, receiving the 3D model may include receiving a request to distinguish between at least two defined volatile compounds (VCs); and determining the first type of 3D elements and the second type of 3D elements may be conducted according to the received request. For example, the request may include selecting the first type of chemiresistor particles to be configured to interact with a first defined major type of VC and the second type of chemiresistor particle to be configured to interact with a second defined major type of VC.

In some embodiments, the method may further include evaporating the solvent from the printed 3D structure. In some embodiments, the evaporation may be conducted after the deposition of each layer, after the deposition of several layers or after the deposition of the entire sensing element. The evaporation may be conducted by one of: conduction heating, heating using a UV lamp, flow of $N_2$ or other gas, naturally in the ambient, using vacuum or any combination thereof.

In some embodiments, electrodes may be added to the deposited sensing element to form a chemiresistor sensor. In some embodiments, the electrodes may be fabricated first (e.g., by lithography process, by printing electronics process and the like) followed by the deposition of the sensing element (e.g., element 130, 130-130C) between the electrodes. Alternatively, the electrodes may be added (e.g., attached) to an already deposited sensing element. In some embodiments, the method may include: adding a first electrode (e.g., electrode 115) having at least one first joint surface (e.g., surface 117) with both at least one of the one or more first type of 3D elements (e.g., elements 132) and at least one of the one or more second type of 3D elements (e.g., elements 132); and adding a second electrode (e.g., electrode 125) having at least one second joint surface (e.g., surface 127) with both at least one of the one or more first type of 3D elements and at least one of the one or more second type of 3D elements. In some embodiments, the electrodes may be added such that first joint surface is different from the second joint surface.

In some embodiments, the method may further include: adding a first electrode (e.g., electrode 110) having at least one first joint surface (e.g., surface 116) with at least one of the one or more first type of 3D elements (e.g., element 134) but not with any one of the one or more second type of 3D elements (e.g., element 132); and adding a second electrode (e.g., electrode 120) having at least one second joint surface (e.g., surface 126) with both at least one of the one or more first type of 3D elements (e.g., elements 134) but not with any one of the one or more second type of 3D elements (e.g., element 132).

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

Various embodiments have been presented. Each of these embodiments may of course include features from other embodiments presented, and embodiments not specifically described may include various features described herein.

The invention claimed is:

1. A sensing element for a chemiresistor sensor comprising:
    one or more first type of 3D elements, each comprising a first type of chemiresistor particles; and
    one or more second type of 3D elements, each comprising a second type of chemiresistor particles,
    wherein surfaces of at least one of the one or more first type of 3D elements are joined to surfaces of at least one of the one or more second type of 3D elements,
    and wherein the first type of chemiresistor particles differ from the second type of chemiresistor particles by at least one of: a type of nanoparticle core and a type of organic ligands bonded to each nanoparticle core, whereby the first and second types of chemiresistor particles can be used to detect different volatile compounds,
    and wherein the one or more first type of 3D elements and the one or more second 3D elements form a multilayered 3D structure.

2. The sensing element of claim 1, wherein the multilayered 3D structure comprises alternating layers each layer comprising either the first or the second type of chemiresistor particles.

3. The sensing element of claim 1, wherein at least one layer in the multilayered 3D structure comprises a chessboard patterned structure made from alternating cube shaped 3D elements each comprising either the first type of chemiresistor particles or the second type of chemiresistor particles.

4. The sensing element according to claim 1, wherein a first nanoparticle core of the first type of 3D elements differs from a second nanoparticle core of the second type of 3D elements by at least one of: a type of conductive material, a size of the nanoparticle core and a shape of the nanoparticle core.

5. The sensing element according to claim 1, wherein the first type of chemiresistor particles comprises a first type of organic ligands and the second type of chemiresistor particles comprises a second type of organic ligands.

6. The sensing element of claim 5, wherein the first type of organic ligands differs from the second type of organic ligands by a type of functional groups included in each type of organic ligands.

7. The sensing element according to claim 1, further comprising:
    one or more third type of 3D elements comprising a third type of chemiresistor particles,
    wherein surfaces of the one or more third type of 3D elements are joined to surfaces of at least one of the one or more first and second types of 3D elements, and
    wherein the third type of chemiresistor particles differ from the first and the second types of chemiresistor particles by at least one of: a nanoparticle core and organic ligands bonded to each nanoparticle core, whereby the third, first and second types of chemiresistor particles can be used to detect different volatile compounds.

8. The sensing element according to claim 1, wherein the first type of chemiresistor particles is selected to interact with at least one first major type of volatile compound (VCs) and the second type of chemiresistor particles is selected to interact with at least one second major type of VCs.

9. The sensing element according to claim 1, wherein the first type of 3D elements differs from the second type of 3D elements by porosity between the chemiresistor particles included in each type of 3D element.

10. A chemiresistor sensor, comprising:
two electrodes; and
a sensing element comprising:
   one or more first type of 3D elements, each comprising a first type of chemiresistor particles;
   and one or more second type of 3D elements, each comprising a second type of chemiresistor particles,
   wherein surfaces of at least one of the one or more first type of 3D elements are joined to surfaces of at least one of the one or more second type of 3D elements,
   and wherein the first type of chemiresistor particles differ from the second type of chemiresistor particles by at least one of: a type of nanoparticle core and a type of organic ligands bonded to each nanoparticle core, whereby the first and second types of chemiresistor particles can be used to detect different volatile compounds,
   and wherein the one or more first type of 3D elements and the one or more second type of 3D elements form a multilayered structure.

11. The chemiresistor sensor of claim 10, wherein:
a first electrode of the two electrodes has a surface that is joined to surfaces of both at least one of the one or more first type of 3D elements and at least one of the one or more second type of 3D elements; and
a second electrode of the two electrodes has a surface that is joined to surfaces of both at least one of the one or more first type of 3D elements and at least one of the one or more second type of 3D elements.

12. The chemiresistor sensor of claim 10, wherein
a first electrode of the two electrode has a surface that is joined to surfaces of at least one of the one or more first type of 3D elements but not with any one of the one or more second type of 3D elements; and
a second electrode of the two electrodes has a surface that is joined to surfaces of at least one of the one or more first type of 3D elements but not with any one of the one or more second type of 3D elements.

* * * * *